(12) United States Patent
Fitz

(10) Patent No.: US 6,890,303 B2
(45) Date of Patent: May 10, 2005

(54) IMPLANTABLE DEVICE FOR MONITORING ANEURYSM SAC PARAMETERS

(76) Inventor: Matthew Joseph Fitz, 1425 Coop St., Encinitas, CA (US) 92024

(*) Notice: Subject to any disclaimer, the term of this patent is extended or adjusted under 35 U.S.C. 154(b) by 275 days.

(21) Appl. No.: 10/116,782

(22) Filed: Apr. 4, 2002

(65) Prior Publication Data

US 2002/0183629 A1 Dec. 5, 2002

Related U.S. Application Data

(60) Provisional application No. 60/294,959, filed on May 31, 2001.

(51) Int. Cl.$^7$ ................................................. A61B 5/00
(52) U.S. Cl. ........................ 600/486; 600/488; 600/485
(58) Field of Search ................................ 600/488, 561, 600/549, 309, 486, 45, 504, 65, 505

(56) References Cited

U.S. PATENT DOCUMENTS

| | | | | |
|---|---|---|---|---|
| 4,846,191 A | * | 7/1989 | Brockway | |
| 5,040,536 A | * | 8/1991 | Riff | |
| 5,924,997 A | * | 7/1999 | Campbell | 600/549 |
| 5,935,084 A | * | 8/1999 | Southworth | 600/561 |
| 5,967,986 A | * | 10/1999 | Cimochowski | |
| 5,987,352 A | * | 11/1999 | Klein | |
| 6,106,476 A | * | 8/2000 | Corl | |
| 6,106,477 A | * | 8/2000 | Miesel et al. | 600/486 |
| 6,140,740 A | * | 10/2000 | Porat | |
| 6,159,156 A | * | 12/2000 | Van Bockel | 600/485 |
| 6,234,073 B1 | * | 5/2001 | Dieso et al. | 99/538 |
| 6,237,398 B1 | * | 5/2001 | Porat et al. | |
| 6,264,611 B1 | * | 7/2001 | Ishikawa | |
| 6,277,078 B1 | * | 8/2001 | Porat et al. | 600/486 |
| 6,416,474 B1 | * | 7/2002 | Penner et al. | 600/309 |
| 6,645,143 B2 | * | 11/2003 | VanTassel et al. | 600/300 |
| 6,652,464 B2 | * | 11/2003 | Schwartz et al. | 600/486 |
| 6,669,647 B2 | * | 12/2003 | Letort et al. | 600/486 |
| 6,682,490 B2 | * | 1/2004 | Roy et al. | 600/486 |
| 2002/0120200 A1 | * | 8/2002 | Brockway et al. | 600/486 |

OTHER PUBLICATIONS

Baum et. al, Aneurysm sac pressure measurements after endovascular repair of abdominal aortic aneurysms, Journal of Vascular Surgery vol. 33 No. 1 pp. 32–41.

* cited by examiner

*Primary Examiner*—Robert L. Nasser

(57) ABSTRACT

A device for measuring physiological parameters within an aneurysm sac that has been excluded from blood flow by an endoprosthesis. The device is comprised of at least two sensors, one placed in the aneurysm sac and another in a systemic artery. A differential between the readings of the two sensors can then be calculated, making the device easily calibrated in vivo and insensitive to changes in atmospheric pressure.

12 Claims, 4 Drawing Sheets

IMPLANTABLE DEVICE FOR MONITORING ANEURYSM SAC PARAMETERS

CROSS-REFERENCE TO RELATED APPLICATIONS

Figure 1:
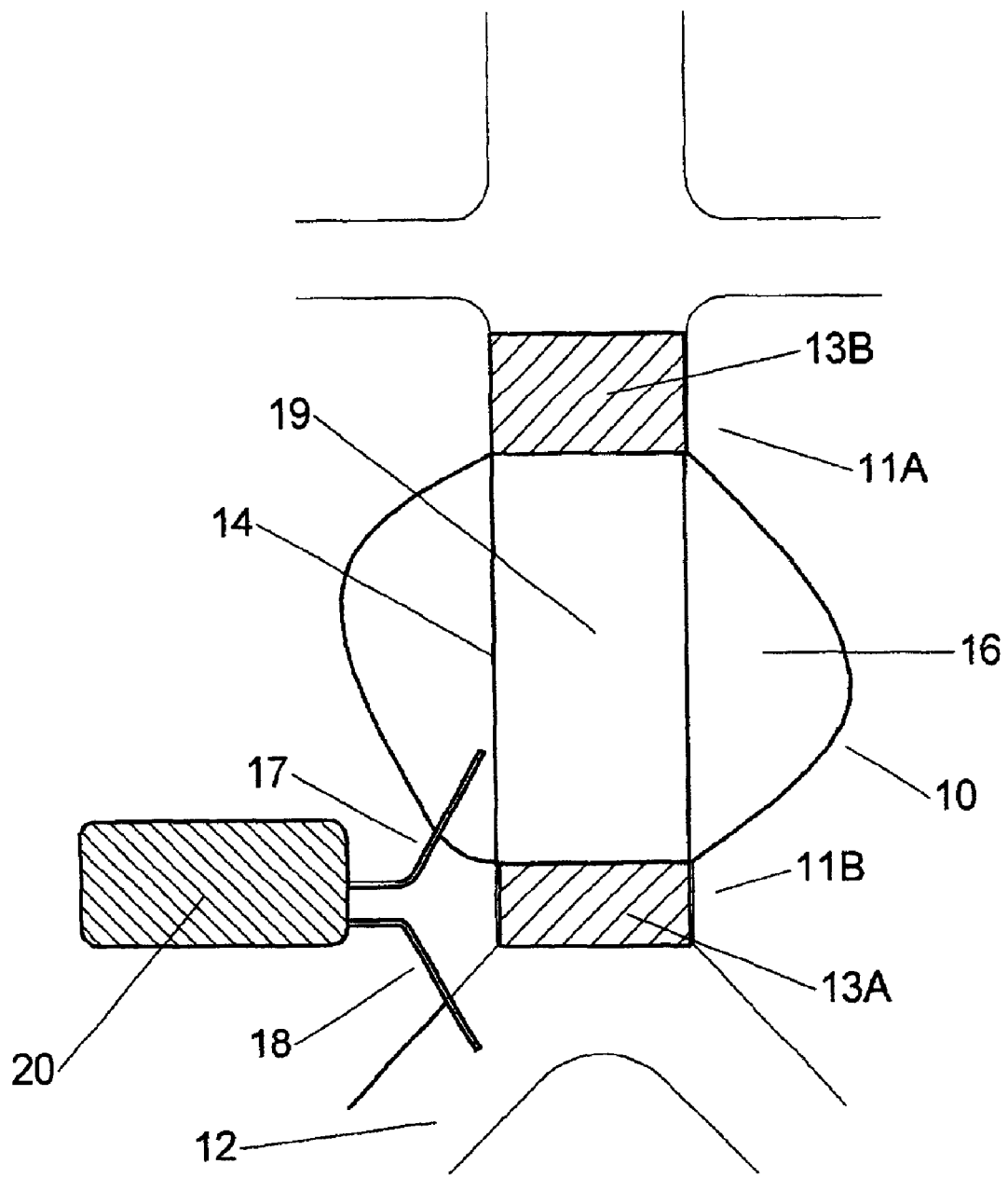

This application is entitled to the benefit of Provisional Patent Application Ser. No. 60/294,959 filed May 31, 2001.

BACKGROUND

1. Field of Invention

The invention relates to a device for introduction into a human body for the purpose of measuring and/or monitoring physiological parameters such as pressure, pressure waveform, or fluid flow rate. This invention is particularly useful for chronic monitoring of physiological parameters within the sac of an aneurysm.

2. Description of Prior Art

In the arteries of human bodies one of the major problems is the loss of strength of the wall of arteries, which can result in aneurysm formation. An aneurysm may endanger the health of a patient because of the risk of internal bleeding which often results in the death of the patient. Therefore, aneurysms are often treated before rupture occurs by minimally invasive implantation of devices such as endovascular prostheses, sometimes called stent-grafts or endoprotheses, which isolate the aneurysm sac from fluid conveyance and thus exclude the aneurysm sac from the circulation.

Such endoprostheses are well known to the person skilled in the art. Although the procedure can be safely performed now, endoleakage is still a major problem immediately following the operation as well as many months or years following the procedure. Endoleakage is the incomplete sealing of the aneurysm sac by the endoprosthesis. Because the aneurysm sac is isolated from fluid conveyance by the endoprosthesis, inflowing blood has no exit path, resulting in a pressure build-up within the aneurysm sac. Monitoring endoleakage is usually performed by non-invasive visualization of the endoleakage by, for example, a CT-scan magnetic resonance, duplex ultrasound, and the like. These non-invasive methods require the patient to frequently return to a hospital or imaging center at substantial expense. In addition, the patient may suffer from a ruptured aneurysm sac caused by an endoleak that develops or worsens between non-invasive monitoring periods. Finally, because of limitations with these current non-invasive monitoring systems, failure to visualize an endoleak does not exclude the presence of such an endoleak. Thus, without a visible endoleak, the aneurysm sac can still be under pressure with the danger of ultimate rupture and internal bleeding.

Baum et. al. in the *Journal of Vascular Surgery* Vol. 33 No. 1 pages 32–41 incorporated herein by reference describes a translumbar sac puncture technique for measuring aneurysm sac pressure. Baum describes accessing the aneurysm sac with a needle and a 5 Fr (1.7 mm internal diameter) sheath through the patient's back. The needle is removed and the aneurysm sac pressure measured through the sheath lumen with a pressure transducer. This technique suffers from several drawbacks:

First, Baum is invasive and must be performed by a physician in a clinical setting. This requires the patient to return to the clinic on a regular basis (Baum suggests every six months on page 39) similar to the non-invasive monitoring schedule described above.

Second, the pressure transducer or sensor (both terms will be considered synonymous throughout) Baum describes must remain outside the patient so that the transducer can be "zeroed" to compensate for atmospheric pressure and periodically calibrated to account for time-dependent drift.

U.S. Pat. No. 6,159,156 to van Bockel discloses a device comprised of a pressure sensor, transducer, telemetry system, and power source implanted entirely within the aneurysm sac through an arterial catheter. However, van Bockel imposes several limitations:

First, the device van Bockel describes is energized using a magnetic or electrical field. Energizing the device in this fashion would require the patient with to charge it frequently from a fixed base station, this would be very inconvenient. In addition, many patients have co-morbidities that require additional implants such as a pacemaker or defibrillator. These devices are known to be sensitive to the magnetic and electrical fields required to energize the transducer.

Second, if a battery were used, the small size van Bockel describes would severely limit the life of the device, requiring frequent battery replacement over the patient's lifetime. Since the device is entrapped between the endoprosthesis and the aneurysm artery wall, replacing the battery would involve an open-abdomen surgical procedure, negating the advantage of the original endovascular procedure.

Third, the small size of the van Bockel's device necessarily limits the memory capacity, the gain of the transducer, and the transmission strength of the transponder.

Fourth, the van Bockel's device must be implanted into the aneurysm before the endoprosthesis is implanted, allowing the opportunity for the device to dislodge from the aneurysm sac.

Fifth, because van Bockel's device is entrapped within the aneurysm sac, it cannot be removed or replaced if it malfunctions, becomes fouled with thrombus (clotted blood), or needs to be calibrated, without an open-abdomen surgical procedure.

Finally, the device disclosed by van Bockel has no means for compensating for changes in atmospheric pressure (so-called "zeroing" the transducer). Since the pressure measurement in question may be on the order of 20 mm Hg (0.4 PSI or $2.67*10^3$ Pa), failure to account for atmospheric pressure would make the error a large percentage of the pressure measurement.

U.S. Pat. No. 5,967,986 to Cimochowski; U.S. Pat. No. 6,237,398 B1 and U.S. Pat. No. 6,277,078 B1 to both Porat; all three incorporated herein by reference, disclose devices for measuring pressure and flow attached to stents and stent-grafts. However, both Cimochowski and Porat disclose devices with sensors placed within the blood flow, rather than within an aneurysm sac. Thus, these devices would be of little use for monitoring aneurysm sac pressure.

U.S. Pat. No. 6,033,366 to Brockway discloses an implantable pressure measurement device consisting of a fluid-filled catheter within an artery connected to a sealed electronics package outside the artery. The electronics package contains a transducer, signal processing chip, telemetry circuit, and power source. Although useful in a laboratory setting in an animal model, the Brockway's device would suffer from several limitations if used to measure aneurysm sac pressure:

First, the Brockway requires a surgical procedure (see also U.S. Pat. No. 4,846,191 Brockway 1989) to be implanted. Although possible in an animal model, in a human implantation of the device as Brockway describes would require an open-abdomen surgical procedure. In U.S. Pat. No. 4,846,191 Brockway describes implanting the catheter of his device into the descending aorta through a femoral access, followed by subcutaneous implantation of the housing. However, this would not be practical for pressure measurements in a human aneurysm sac because it would require placing the catheter between the endoprosthesis and the aorta, which itself would be a source of endoleak. In addition, the femoral access Brockway describes requires ligation of the femoral artery. In a human patient, this would lead to loss of the lower portion of the ligated limb.

Second, Brockway accounts for atmospheric pressure by using a second, external device (i.e. outside the patient's body) to measure the atmospheric pressure and perform the appropriate subtraction. Therefore, the device could provide an accurate measurement only when the patient is in proximity to the external device, assuming that the external device was calibrated frequently to account for shifts in the atmospheric pressure caused by changing weather patterns.

Third, the Brockway has no means of calibration to account for drift in the transducer except to surgically remove the transducer and replace it with a new transducer.

U.S. Pat. No. 6,106,476 to Corl incorporated herein by reference discloses a miniature pressure sensor mounted on a 0.014–0.018" wire. As Corl depicts in FIG. 1 of U.S. Pat. No. 6,106,476; his device is not intended as a chronic implant because, as Brockway teaches in U.S. Pat. No. 4,846,191; devices based on miniature solid state sensors such as Corl's "require calibration within a short time prior to use and are suitable only for acute measurements". Corl's pressure sensing wire also would be unable to account for variations in atmospheric pressure unless part of the device remained outside the body as he depicts in '476. Therefore, while providing benefits over Brockway such as reduced diameter and kink resistance, Corl's device would not be suitable for chronic measurement of pressure within an aneurysm sac.

SUMMARY OF THE INVENTION

The present invention is a device capable of sensing pressure, a pressure waveform, and/or blood flow, within an aneurysm sac substantially excluded from fluid conveyance by implantation of an endoprosthesis.

The device according to the present invention is characterized by a first sensor or transducer disposed within the aneurysm sac and a second sensor or transducer disposed within an artery subjected to systemic (i.e. physiologic) blood pressure and flow. The sensors are attached at least one implantable housing assembly.

Objects and Advantages

Several object and advantages of the implantable monitoring device of the present invention are:

(a) to provide a means for measuring physiologic data such as pressure, pressure wave form, and/or flow rate especially within an aneurysm sac (b) to provide a device that can be chronically implanted in the body of a patient (c) to provide a device that can be implanted without a major surgical procedure (d) to provide a device that will monitor, record, analyze, and/or report physiologic data (e) to provide a device with a means for compensating for changes in atmospheric pressure (f) to provide a means for pressure measurement that does not require a second external device to compensate for atmospheric pressure (g) to provide a means for calibrating a plurality of sensors in vivo These objects and advantages will become apparent from a consideration of the ensuing description and drawings.

DRAWING FIGURES

To further clarify the invention, exemplary embodiments of a device and a set according to the present invention will be described hereafter, with reference to the drawings.

Figure 2:
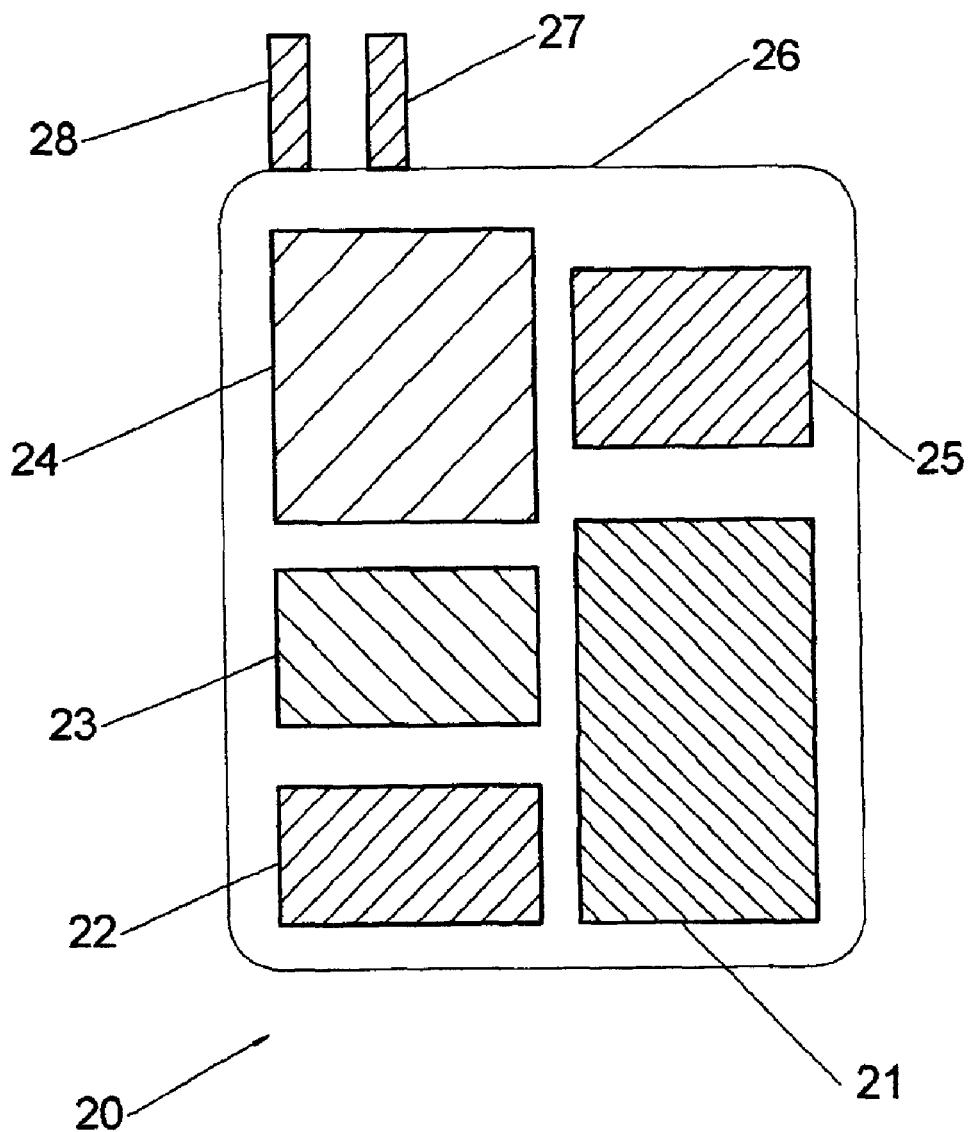
Figure 4:
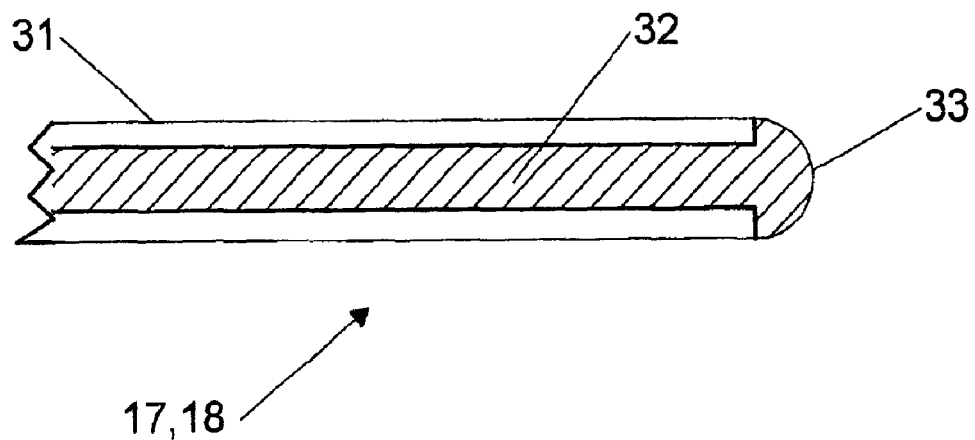
Figure 3:
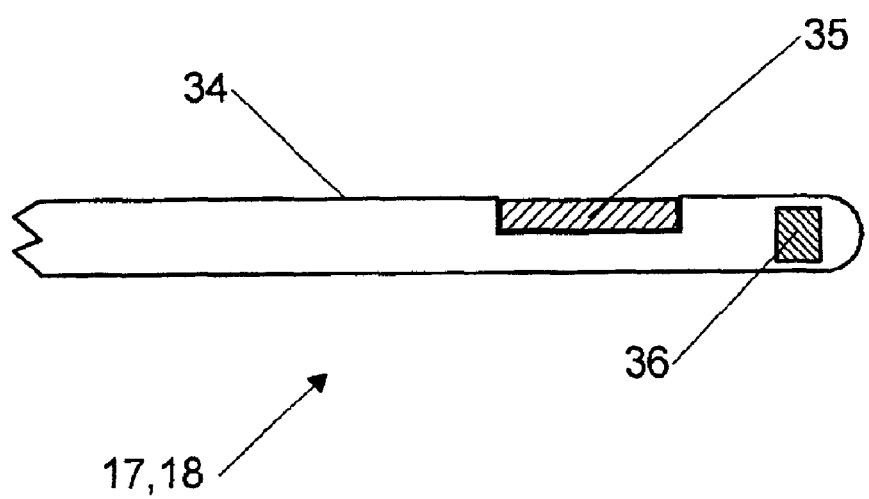
Figure 5:
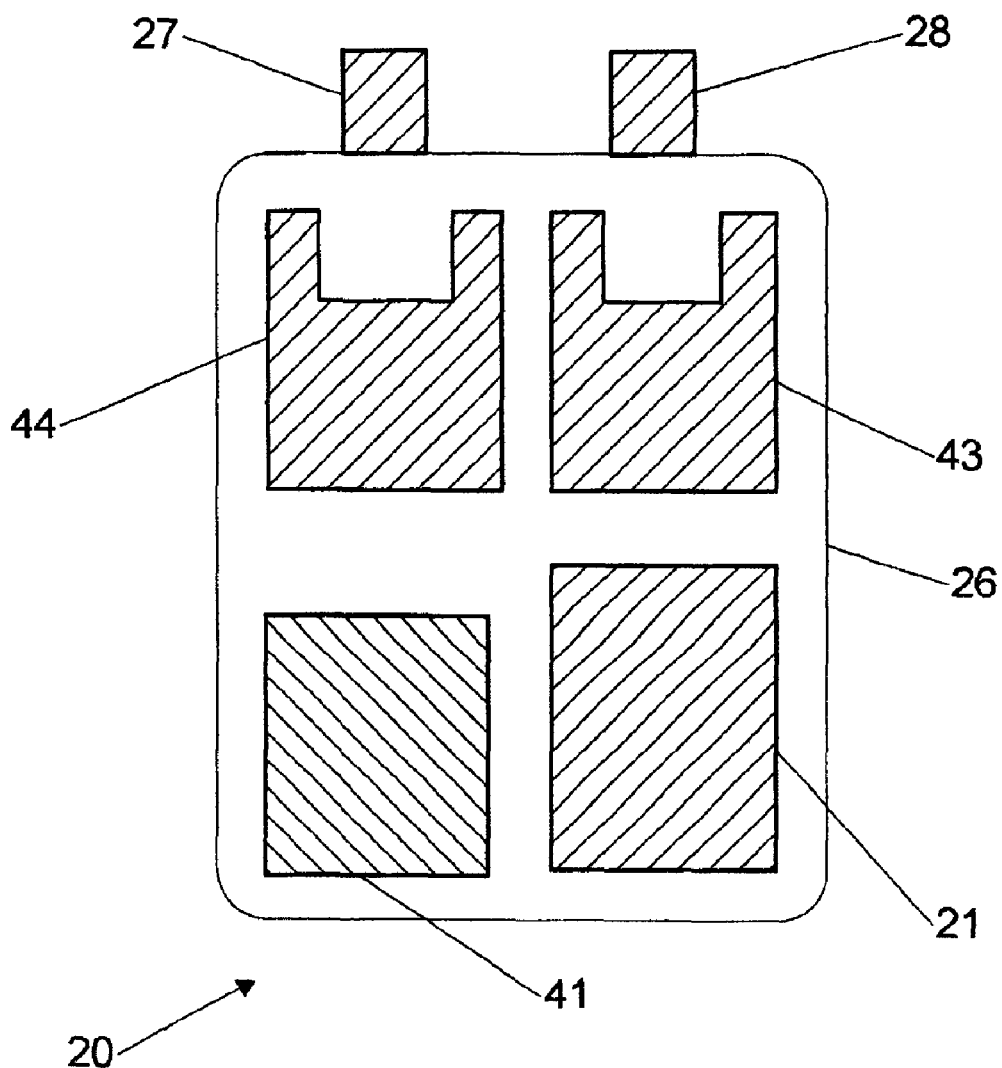

FIG. 1 schematically shows the aneurysm monitoring device according to the present invention, positioned in an aneurysm sac that is excluded from the circulation by an endoprosthesis;

FIG. 2 schematically shows a housing assembly of the present invention in a first embodiment;

FIG. 3 schematically shows the distal end of a sensor in a first embodiment;

FIG. 4 schematically shows the distal end of a sensor in a second embodiment;

FIG. 5 schematically shows a housing assembly of the present invention in a second embodiment;

In the description corresponding parts have corresponding reference signs. Measurements and values, as well as the specific embodiments are merely presented as examples and are not to be interpreted as limiting the scope of the present invention.

DETAILED DESCRIPTION OF THE PREFERRED EMBODIMENTS

An aneurysm is dangerous to the health of a human since rupture of an aneurysm would lead to internal bleeding with possible lethal consequences. In order to negate this risk endoprosthesis are used for bridging the aneurysm. In FIG. 1 a tube endoprosthesis 19 is shown, bridging aneurysm 10. The endoprosthesis 19 comprises a flexible closed wall 14, and is provided fully or at both ends with a stent 13A, 13B. A first end of the endoprosthesis 11A is positioned at the upstream side of the aneurysm 10, by means of the stent 13B, a second end 11B at the opposite, downstream side of the aneurysm 10 by means of the second stent 13A. Endoprostheses of this type are known in the state of the art and are for example manufactured under the registered trademarks Ancure by Guidant Corporation, Zenith by Cook Corporation, and Excluder by W L Gore. However, all kinds of endoprosthesis can be used, for example a tube, bifurcated, unibody, or bilateral prosthesis.

FIG. 1 shows a first sensor 17 disposed inside an aneurysm sac 16. The first sensor 17 can be of any suitable type, for example piezoelectric, acoustic, membrane, strain gauge operated or the like. Examples of suitable sensors are disclosed in U.S. Pat. Nos. 6,264,611 and 6,140,740 both incorporated herein by reference. A second sensor 18 is shown in FIG. 1 placed within an artery 12 outside the aneurysm sac 16. The second sensor 18 may be of the same type as first sensor or may be of a different type. The measurement range for both the first and second sensors is sufficient to measure normal and high physiologic pressures and/or flow rates in the aneurysm sac 16 and in the artery 12 outside the aneurysm sac. A suitable range and sensitivity of both the first sensor and the second sensor can be readily chosen by the person skilled in the art.

In the preferred embodiment shown in FIG. 1, the first sensor 17 and second sensor 18 connect to a single housing assembly 20. In an alternative embodiment (not shown) of the present invention, the first sensor 17 and second sensor 18 each connect to separate housings.

FIG. 2 shows the first embodiment of the present invention with the housing 26 enclosing a power source 21, a signal processor 24, a telemetry circuit 25, a data processor 23, and a data storage device 22. Connectors 27, 28 are provided for the first sensor 17 and the second sensor 18. The housing 26 is hermetically sealed and constructed of a biocompatible material. All of these items are articles of commerce and are known to persons skilled in the art.

FIG. 3 shows the first embodiment of the first sensor 17 and/or the second sensor 18. The distal end of a sensor wire 17, 18 contains a pressure sensor 35, a transducer flow rate sensor 36, or both elements. The proximal end of the sensor wire (not shown) contains a connector to connect the sensor wire 17, 18 to the housing assembly 20. The sensor wire 17, 18 is constructed from a biocompatible material and is typically of a wire core-and-hypotube design known in the art and is preferably less than 0.080" (2 mm) in diameter. Wires or probes incorporating pressure and/or flow rate sensors are known within the state of the art and there are many design possibilities.

FIG. 4 shows an alternative embodiment of the first sensor 17 and/or second sensor 18 made of a catheter 31 filled with pressure a transmitting media 32 covered by a gel or membrane 33. The catheter 31 connects to the pressure sensor 43, 44 via connectors 28, 27 at the catheter's 31 proximal end (not shown). The catheter 31 may constructed from a variety of biocompatible materials and is preferably less than 0.080" (2 mm) diameter. An illustrative example of this type of catheter is described in U.S. Pat. No. 6,033,366 incorporated herein by reference. However, pressure sensitive catheters are known within the state of the art and there are many other design possibilities.

FIG. 5 shows an alternative embodiment of the housing assembly 20 with a housing 26 enclosing the power source 21, the device processors and associated electronic combined on an integrated microchip 41, and pressure transducers 43, 44.

Operation (a) Implanting the Device

To implant the sensors 17, 18 the patient is positioned prone on a catheterization laboratory table. Using fluoroscopic guidance, a physician introduces a needle of a gauge appropriate to the diameter of the first sensor 17 through the skin and tissue of the patient's back near the midline until the needle penetrates into the aneurysm sac 16. The sensor 17 is fed through the needle until the sensor 17 is within the aneurysm sac 16. The needle is removed.

Next, a needle is introduced through the skin and tissue of the patient near a non-aneurysm artery 12. In the preferred embodiment, this puncture is near the first puncture site for example in the iliac or femoral artery. In an alternative embodiment (not shown) in which two independent housings are employed, any convenient puncture site can be used. When the needle is positioned within the selected artery 12, the second sensor 18 is introduced through the needle into the artery 12. The needle is removed.

The first and second sensors 17, 18 are connected to the connectors 27, 28. The housing assembly 20 is subcutaneously implanted in, for example, the back using surgical techniques known in the medical art.

Those skilled in the art will recognize a wide variety of potential catheter, sheath, or needle designs that could be used to facilitate introduction of the sensors 17, 18 into the aneurysm sac 16 and/or the artery 12. These and many similar variations are considered to fall within the scope of the present invention.

(b) Compensating for Atmospheric Pressure

The pressure of interest within the aneurysm sac 16 is not an absolute pressure, but rather a differential pressure between the patient's systemic (physiologic) blood pressure and the pressure within the aneurysm sac 16. The second sensor 18 acts as a reference for the first sensor 17 and subtraction of the two pressures by the data processor 23 determines the pressure differential. Because both the first and second pressure sensors 17, 18 are at the same atmospheric pressure, the device of the present invention is relatively insensitive to changes in atmospheric pressure.

(c) Calibrating the Sensors

Systemic blood pressure is routinely determined using non-invasive techniques for example the acoustic cuff measurement. Using non-invasive techniques, the systemic blood pressure is measured as a reference and transmitted to the data processor 23 or 41 by means of the wireless telemetry circuit 25 or 41. The data processor 23 reads a pressure differential between the first and second sensors 17, 18 and records the information in the data storage device 22 or 41. The data processor 23 or 41 then uses the reference systemic blood pressure information to calibrate the second sensor 18 which is implanted in the artery 12 exposed to systemic blood pressure. The data processor 23 or 41 then retrieves the last recorded pressure differential between the first and second sensors 17, 18 from the data storage device 22 or 41 and subtracts the differential from the systemic blood pressure reading. The first sensor 17 is then calibrated using the systemic blood pressure and differential values.

Blood flow rates within arteries are also routinely determined using non-invasive techniques for example ultrasound measurements and could be used to determine a reference flow rate. For flow rate sensors, the algorithm described in the preceding paragraph would also be used. The blood flow rate in artery 12 containing the second sensor 18 would be used to calibrate the second sensor 18. The differential in flow rates between the first and second sensors 17, 18 would be used to calibrate the first sensor 17.

The preceding description of the calibration method presented as an example. Those skilled in the art of will recognize that there are a variety of possible algorithms based on comparing the data from the in vivo sensors to a reference value. These and many similar variations are considered to fall within the scope of the present invention.

(d) Physiologic Data Measurement

An objective of the present invention is to monitor the physiological parameters within of the aneurysm sac 16 excluded from circulation by an endoprosthesis 19. To this end, the first sensor 17 reads the pressure, pressure wave form, and/or blood flow rate. This data can then be stored in the data storage device 22 or 41, transmitted on a continuous or periodic basis by means of the wireless telemetry circuit 25 or 41 to an external computer (not shown) or through a telephone or cellular telephone (not shown) to the physician or through the Internet to the physician or a central monitor, or analyzed by the data processor 25 or 41 or an external computer. Furthermore, a wide variety of algorithms could be used to warn the patient or physician of a dangerous condition. For example, the data processor 25 or 41 could be programmed to transmit a warning if the pressure within the aneurysm sac 16 as measured by the first sensor 17 reached a pre-determined percentage of the systemic blood pressure as measured by the second sensor 18 or if the pressure or flow rate within the aneurysm sac 16 reached a pre-determined value or if the frequency of the pressure wave form were to become pulsatile, or a combination of these conditions. These and many similar variations are considered to fall within the scope of the present invention.

Advantages

From the description above, a number of advantages of my aneurysm monitoring device become evident:

(a) The device can be implanted with a simple, minor surgical procedure.

(b) The device is relatively insensitive to changes in atmospheric pressure. This allows accurate readings if for example the patient were in an airplane or lived at an altitude significantly different from the clinic where the device was implanted.

(c) The device can be calibrated in vivo by using data from less-invasive or non-invasive measurements. This reduces the probability of errors caused by drift or malfunction in the sensors.

(d) The device can provide data concerning the conditions within the excluded aneurysm sac that can be used to alert the patient and physician to a life-threatening aneurysm rupture. This could allow earlier intervention than annual or semi-annual imaging allows and could save the life of the patient.

(e) The data provided by the monitoring device is easier to interpret than more subjective imaging data and can be more easily processed by a computer. This allows for more accurate leak detection and reduces the probability of a false negative or positive created by the image method. In addition, the data interpretation and warning signals can be automated, freeing the physician to concentrate on other issues.

(f) The monitoring device has the potential to replace the current routine of annual or semi-annual imaging that patients with endoprosthesis are required to endure. Not only does this save the patient from inconvenience and stress, but could save the healthcare system significant resources.

Conclusion, Ramifications, and Scope

Accordingly, the reader will see that the aneurysm sac monitoring system of this invention can be used to accurately and reliably report physiologic conditions within an aneurysm sac that has been excluded by an endoprosthesis. Because the device can be packaged to a small size, it can be easily implanted and is relatively unobtrusive to the patient. Furthermore, the atmospheric compensation and calibration features of the monitoring system allow a variety of sensor designs to be used.

Although the description above contains many specifications, these should not be construed as limiting the scope of the invention but as merely providing illustrations of some of the presently preferred embodiments of this invention.

For example, the housing can be constructed of any biocompatible material such as metal, plastic, or foam.

For example, the connectors to attach the sensors to the housing assembly could be male or female, protruding or recessed, electrical connectors or mechanical couplings.

For example, the power source could be a battery, energizing transponder, piezoelectric-electric generator that uses the pulse of the heart beat to charge, or the like.

For example, the device need not incorporate an on-board data storage device, but could transmit the data to an external data storage device.

For example, the device need not incorporate an on-board data processor, but could transmit the data to an external data processor.

For example, the data storage device, data processor, telemetry circuit, and/or signal processor could be integrated on a single chip or onto multiple chips by methods known to those skilled in the art.

For example, the sensors need not be based on semiconductor, ultrasound, or catheter systems but could also be piezoelectric, acoustic, membrane, strain gauge operated or the like.

For example, the method of calibrating the sensors could utilize a variety of algorithms known to those skilled in the art such as proportional control, integral control, and/or derivative control.

For example, the reference measurements taken from the patient to calibrate the sensors could be collected by a variety of invasive, minimally invasive, or non-invasive means.

For example, the data could be transmitted at a variety of time periods such as in a continuous transmission or transmission only by an external command.

For example, the data could be transmitted by a number of means such as by radio wave, telephone, cellular phone, Internet, and the like.

For example, the data could be analyzed in a multitude of ways such as analysis of pressure differentials, flow rate differentials, absolute pressure or flow rate, wave form parameters including pulsation or lack or pulsation, or a combination of these factors.

For example, the sensors need not be implanted with a needle, but could also be implanted with a catheter, sheath, probe, or similar device known in the art.

For example, the housing or multiple housings could be implanted in a variety of areas in the body.

For example, the first and second sensors could each be connected to separate housings to allow the second sensor to be implanted in any artery. The electronics of each device could then communicate with each other directly or with an external device.

For example, a plurality of sensors could be used with multiple sensors in the aneurysm sac and/or sensors in a plurality of arteries. These sensors then could be connected to the same housing or to multiple housings.

Thus the scope of the invention should be determined by the appended claims and their legal equivalents, rather than by the examples given.

I claim:

1. A method of calibrating at least two sensors disposed within a human body, comprising:
   a. measuring a physiological parameter in said human body to obtain a reference value for said physiological parameter,
   b. providing a first sensing means disposed within an aneurysm sac,
   c. providing a second sensing means disposed within an artery outside of said aneurysm sac,
   d. providing a means for calculating a differential value between said first sensing means and said second sensing means,
   e. providing a means for synchronizing said second sensing means with said reference value whereby said second sensing means is calibrated to said reference value,
   f. providing a means for calculating a value of said first sensing means by subtracting said differential value from said reference value.

2. The method of claim 1, wherein said physiological parameter is a pressure.

3. The method of claim 1, wherein said physiological parameter is a flow velocity.

4. The method of claim 1, wherein said physiological parameter is a pressure waveform.

5. The method of claim 1, wherein said first sensing means is disposed within said aneurysm sac by means of fluoroscopic guidance.

6. The method of claim 1, wherein said first sensing means is selected from the group consisting of piezoelectric, semiconductor, catheter, acoustic, and ultrasonic sensors.

7. The method of claim 1, wherein said second sensing means is selected from the group consisting of piezoelectric, semiconductor, catheter, acoustic, and ultrasonic sensors.

8. A method for measuring a physiological parameter in an aneurysm sac, comprising the steps of:

a. chronically implanting a first sensing means within an aneurysm sac, b. chronically implanting a second sensing means within an artery outside of said aneurysm sac, c. calibrating said first sensing means using at least a first signal from said second sensing means, d. measuring said physiological parameter using a signal from the first sensing means and a second signal from the second sensing means.

9. The method of claim 8, wherein said physiological parameter is a pressure.

10. The method of claim 8, wherein said physiological parameter is a flow velocity.

11. The method of claim 8, wherein said physiological parameter is a pressure waveform.

12. The method of claim 8, wherein said first sensing means is selected from the group consisting of piezoelectric, semiconductor, catheter, acoustic, and ultrasonic sensors.

* * * * *